US009977041B2

(12) United States Patent
Yamashita et al.

(10) Patent No.: US 9,977,041 B2
(45) Date of Patent: May 22, 2018

(54) AUTOMATIC ANALYSIS DEVICE

(71) Applicant: HITACHI HIGH-TECHNOLOGIES CORPORATION, Tokyo (JP)

(72) Inventors: Yoshihiro Yamashita, Tokyo (JP); Takaaki Hagiwara, Tokyo (JP); Toshiharu Suzuki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 350 days.

(21) Appl. No.: 14/648,355

(22) PCT Filed: Dec. 3, 2013

(86) PCT No.: PCT/JP2013/082490
§ 371 (c)(1),
(2) Date: May 29, 2015

(87) PCT Pub. No.: WO2014/088004
PCT Pub. Date: Jun. 12, 2014

(65) Prior Publication Data
US 2015/0293135 A1 Oct. 15, 2015

(30) Foreign Application Priority Data

Dec. 5, 2012 (JP) ................................. 2012-266489

(51) Int. Cl.
G06F 11/00 (2006.01)
G01N 35/00 (2006.01)
G01N 35/10 (2006.01)

(52) U.S. Cl.
CPC ... *G01N 35/00722* (2013.01); *G01N 35/0098* (2013.01); *G01N 35/1004* (2013.01); *G01N 2035/00891* (2013.01)

(58) Field of Classification Search
CPC .......................... A61K 2300/00; C12Q 1/6874
(Continued)

(56) References Cited

U.S. PATENT DOCUMENTS

2007/0175284 A1 8/2007 Oonuma et al.
2010/0284862 A1 11/2010 Kakizaki et al.
2010/0291619 A1* 11/2010 Robinson ................. C12Q 1/04
435/34

FOREIGN PATENT DOCUMENTS

CN 101013139 A 8/2007
CN 101965518 A 2/2011

OTHER PUBLICATIONS

Chinese Office Action received in corresponding Chinese Application No. 201380062432.9 dated Mar. 31, 2017.
(Continued)

*Primary Examiner* — Edward Raymond
(74) *Attorney, Agent, or Firm* — Mattingly & Malur, PC

(57) ABSTRACT

It is determined whether an automatic analysis device is in a state where it is necessary to perform periodic cleaning or periodic replacement on a B/F separation passage of a reaction liquid suction nozzle 120 for B/F separation or the like and a detection passage of a reaction liquid suction nozzle 123 for detection, a detection unit 124, and the like, based on the properties of a specimen, a reagent, and a reaction liquid which is obtained by reacting the specimen and the reagent, an analysis protocol which defines treatment conditions of these solutions, and the number of times of dispensing, feeding, and measuring the solutions; and the determined result is displayed on a display 130 as a signal. Accordingly, the automatic analysis device is provided so as to be able to perform adequate maintenance in accordance with analysis conditions.

14 Claims, 5 Drawing Sheets

(58) Field of Classification Search
USPC .......................................... 702/182–185, 14
See application file for complete search history.

(56) References Cited

OTHER PUBLICATIONS

International Preliminary Report on Patentability received in corresponding International Application No. PCT/JP2013/082490 dated Jun. 18, 2015.

* cited by examiner

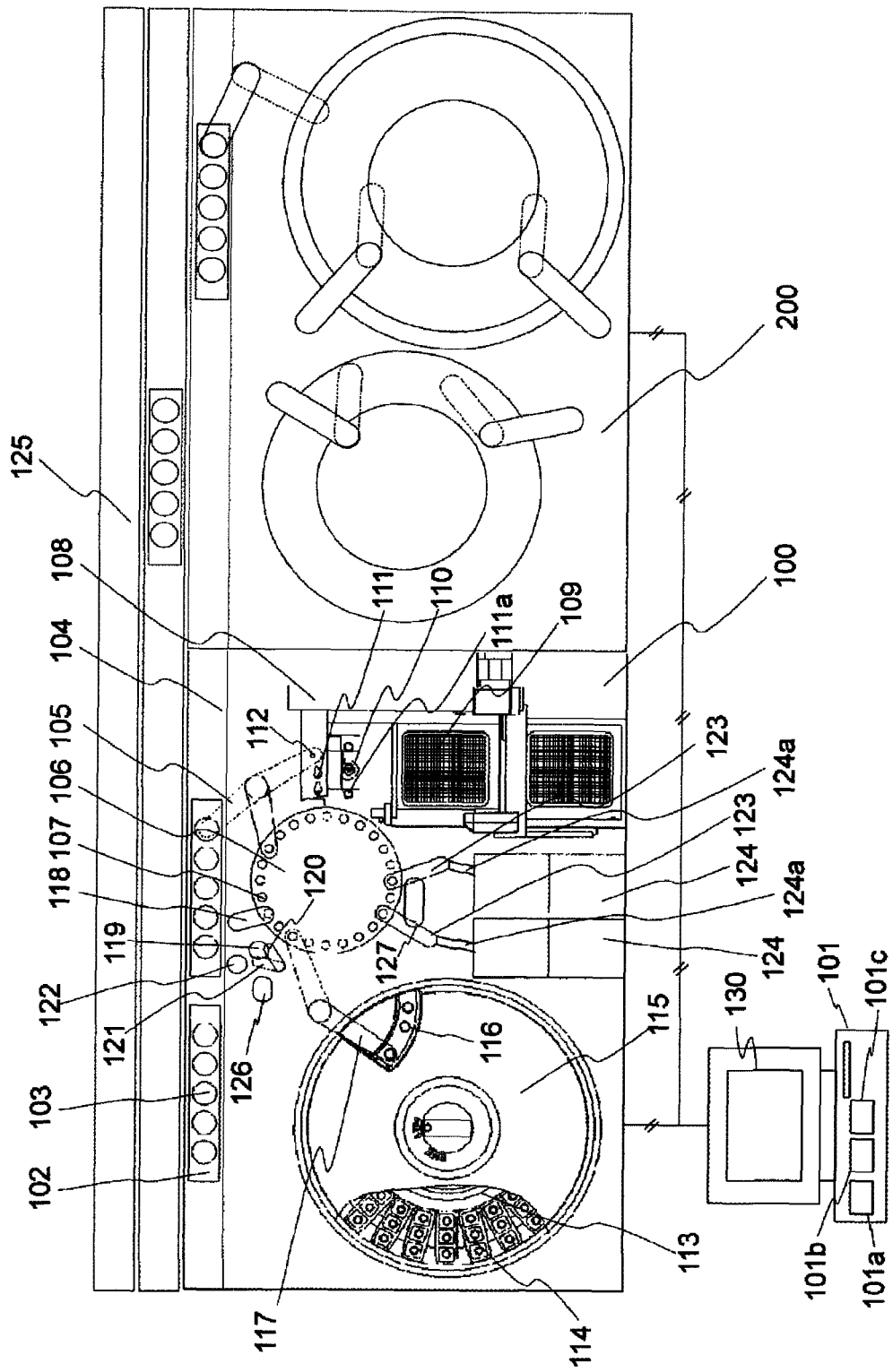
[Fig. 1]

[Fig. 2]
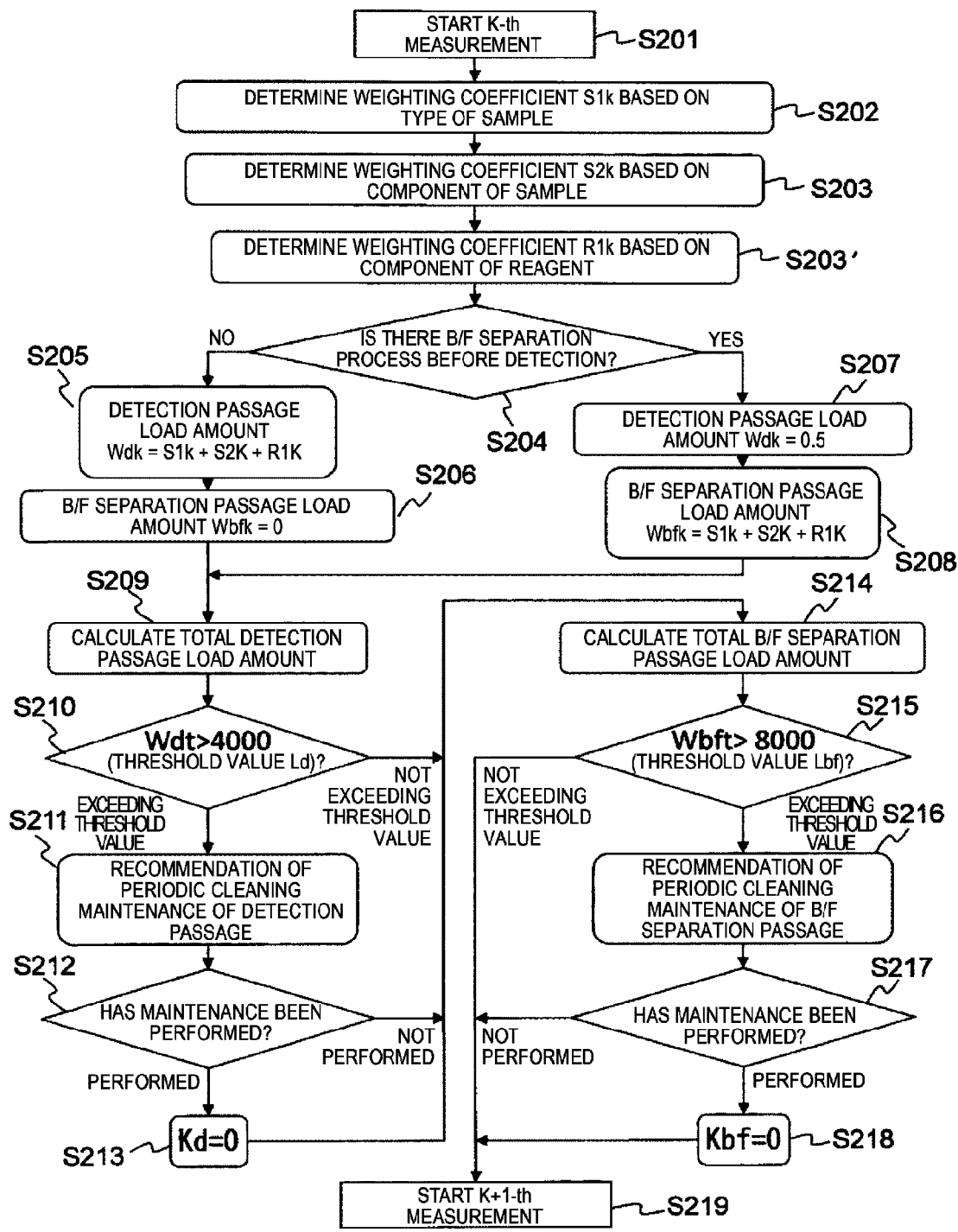

[Fig. 3]
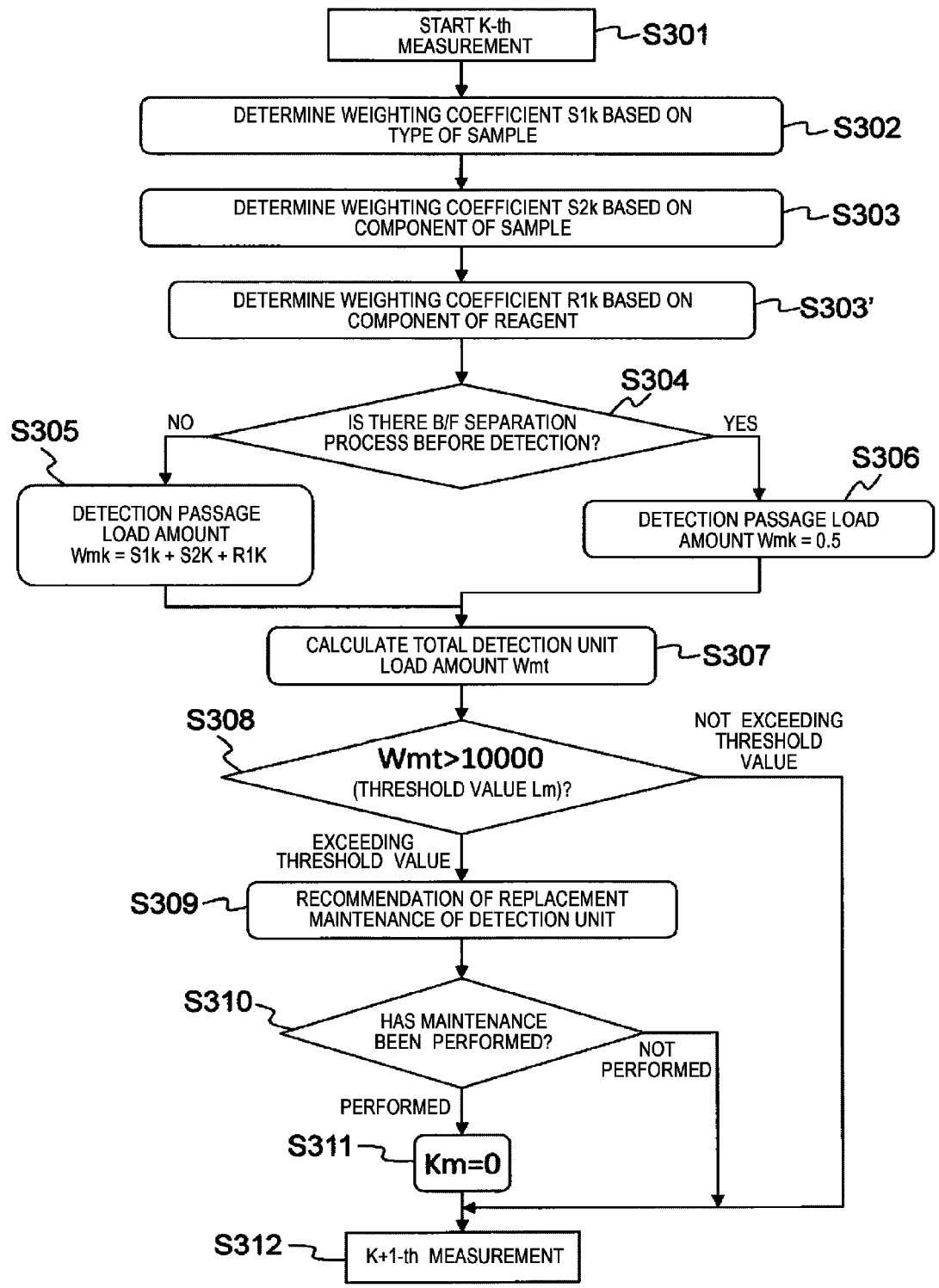

[Fig. 4]
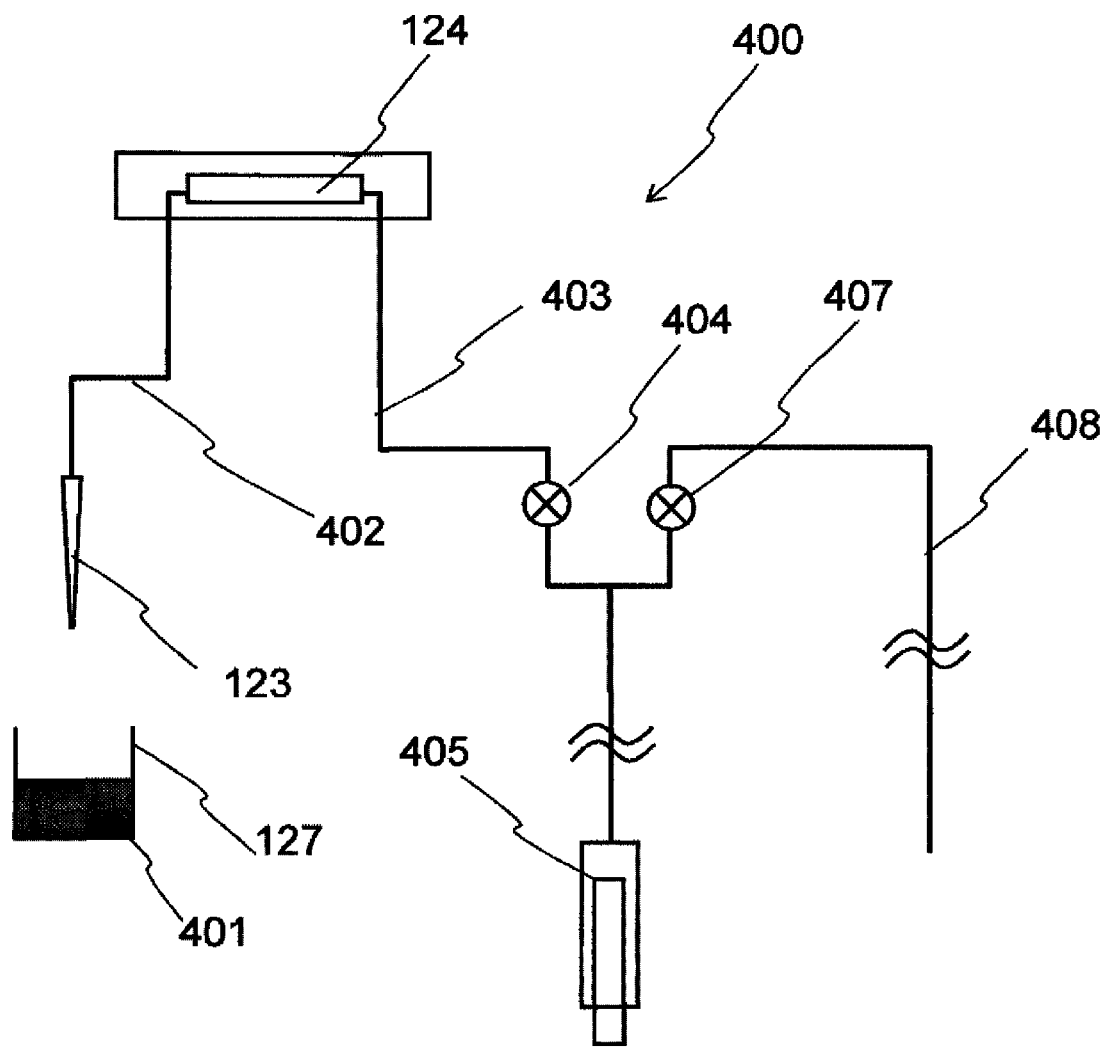

[Fig. 5]
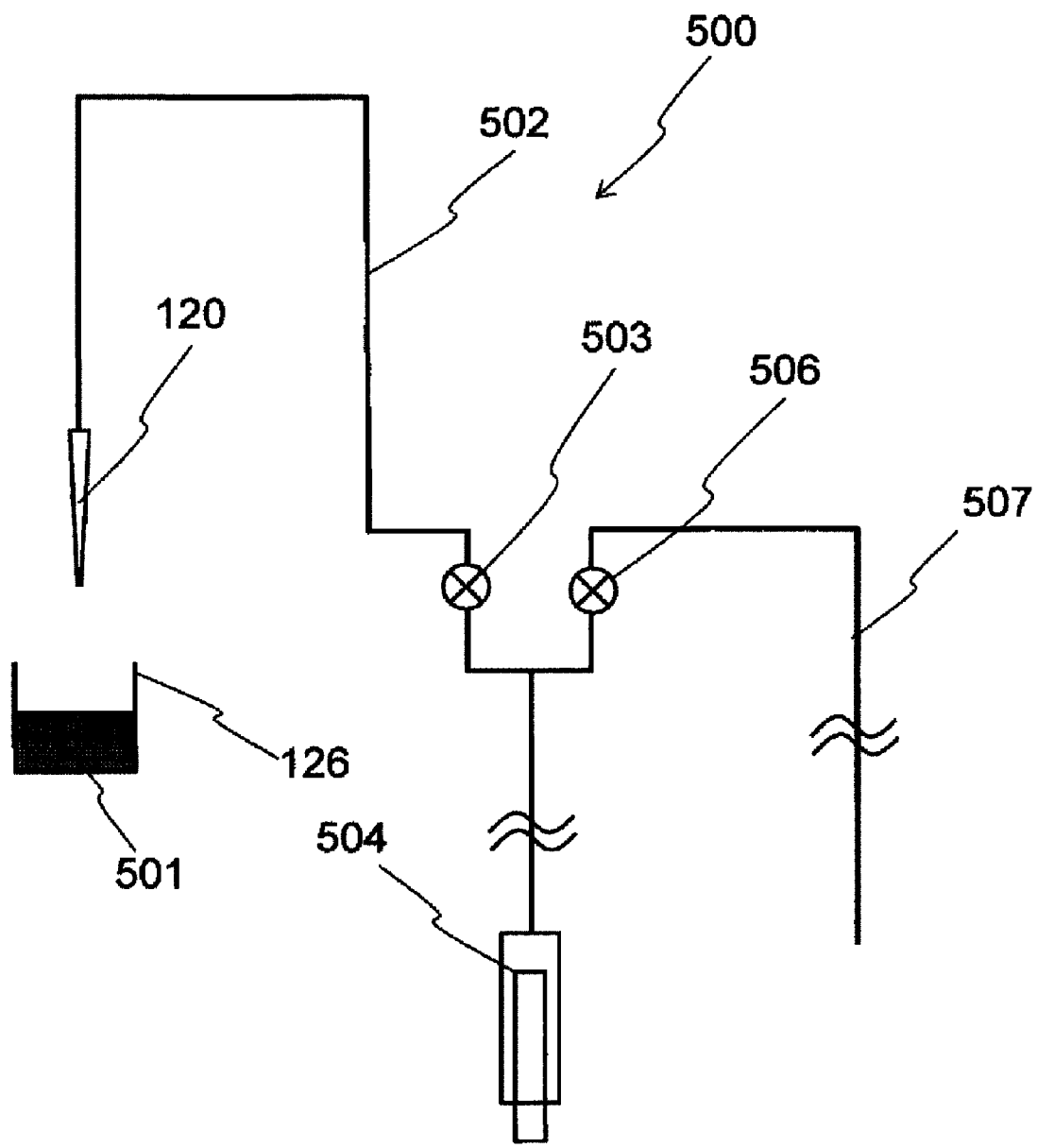

AUTOMATIC ANALYSIS DEVICE

TECHNICAL FIELD

The present invention relates to an automatic analysis device for performing quantitative determination or qualitative determination of a predetermined measurement object which is contained in a specimen such as blood and urine.

BACKGROUND ART

In an automatic analysis device, in order to secure performance of requiring carry-over between specimens even when a sampling frequency or a sampling integrated amount for the specimen becomes large, the specimens are sequentially sampled by a probe, and at least one of a cleaning frequency or a cleaning time when cleaning the probe is changed based on at least one of the sampling frequency or the sampling amount of the specimen by the probe (refer to PTL 1).

CITATION LIST

Patent Literature

PTL 1: JP-A-2007-225608

SUMMARY OF INVENTION

Technical Problem

In an automatic analysis device, examples of members which come into contact with solutions in order to dispense or feed solutions containing a specimen or reagent, and a reaction liquid include a specimen dispensing passage; a reagent dispensing passage; a reaction liquid suction passage in a B/F separation process (process that separates Bound which has been specifically adsorbed to magnetic particles through an antigen-antibody reaction from Free which has been non-specifically and physically adsorbed thereto); a passage for which the reaction liquid is fed to a detection unit and the detection unit which is provided as apart of this passage; a specimen suction passage for electrolyte analysis and an electrolyte measurement unit which is provided as a part of this passage.

In order to maintain analysis performance, it is necessary to perform maintenance such as periodic cleaning or periodic replacement of these members such as the passages, in addition to cleaning the members each time dispensing or feeding a solution occurs.

In general, in the members such as the passages which come into contact with a solution containing a specimen or a reagent, cleaning is performed inside and outside of the passages each time dispensing a solution occurs, using water or a cleanser containing a surfactant or the like, in order to suppress carry-over between specimens or reagents. In contrast, objects for periodic cleaning or periodic replacement of members are generally members such as passages which are affected by long-term contact with a solution including a specimen or a reagent.

For example, since the reaction liquid suction passage in the B/F separation process comes into long-term contact with a solution containing a specimen or a reagent, protein, lipid, or the like derived from the specimen or the reagent is adhered or accumulated on the inside of the passage, and therefore, there is a possibility of blocking the passage. For this reason, it is necessary to periodically clean the inside of the passage using the cleanser containing a surfactant, hypochlorous acid, or the like.

In addition, in regard to a passage which feeds a reaction liquid to a detection unit and the detection unit which is provided as a part of the passage, degradation of analysis performance could occur due to, for example, deterioration in a surface property of a sensor or the like of the detection unit in addition to the blocking of the passage caused by adhesion or accumulation of protein, lipid, or the like derived from a specimen or a reagent. For this reason, it is necessary to perform periodic cleaning or periodic replacement of the detection unit similarly to the above.

In general, the frequency of the above-described periodic cleaning or periodic replacement is defined based on the number of times of measurement or a use period in standard analysis conditions.

However, an adequate maintenance frequency strongly depends not only on the number of times of measurement, but also on the properties of a specimen or the analysis protocol in each measurement. It cannot be said that it is necessary and sufficient to determine the timing for periodic cleaning or periodic replacement based on the standard analysis conditions as in the related art. That is, the frequency of periodic cleaning or periodic replacement which is defined in advance becomes too frequent or too infrequent depending on the analysis conditions, which results in deterioration in usability and analysis performance.

In the automatic analysis device disclosed in the above-described PTL 1, it is possible to determine a timing for cleaning a dispensing probe in order to suppress carry-over between specimens. However, it is impossible to achieve optimization of the frequency of maintenance such as periodic cleaning or periodic replacement of a member such as a passage depending on the analysis conditions.

An object of the present invention is to provide an automatic analysis device in which it is possible to perform adequate maintenance such as periodic cleaning or periodic replacement in accordance with analysis conditions.

Solution to Problem

In order to solve the above-described problem, for example, a configuration disclosed in claims is employed.

The present invention includes a plurality of means for solving the above-described problem, and an example thereof includes an automatic analysis device which measures a specimen such as blood or urine, including: a member which comes into contact with at least any one of solutions including the specimen, a reagent, and a reaction liquid which is obtained by reacting the specimen and the reagent; and a control device which determines whether it is necessary to perform maintenance of the member based on the properties of the solutions, an analysis protocol that defines treatment conditions of the solutions, and the number of times of dispensing, feeding, and measuring the solutions, and outputs the determined result as a display signal.

Advantageous Effects of Invention

According to the present invention, it is possible to provide information so as to perform adequate maintenance such as periodic cleaning or periodic replacement in accordance with various analysis conditions, and therefore, the frequency of the maintenance does not become too frequent or too infrequent, thereby improving usability and securing analysis performance.

BRIEF DESCRIPTION OF DRAWINGS

FIG. 1 is a top view showing an overall configuration of an embodiment of an automatic analysis device of the present invention.

FIG. 2 is a flowchart showing a treatment procedure of determining recommendation of periodic cleaning maintenance in the embodiment of the automatic analysis device of the present invention.

FIG. 3 is a flowchart showing a treatment procedure of determining recommendation of periodic replacement maintenance in the embodiment of the automatic analysis device of the present invention.

FIG. 4 is a view showing an outline of a passage of a detection system passage in the embodiment of the automatic analysis device of the present invention.

FIG. 5 is a view showing an outline of a passage of a B/F separation passage in the embodiment of the automatic analysis device of the present invention.

DESCRIPTION OF EMBODIMENTS

An embodiment of an automatic analysis device of the present invention will be described using FIGS. 1 to 5. In FIGS. 1 to 5, a case where the present invention is applied to an immunoanalysis device as the automatic analysis device will be described as an example.

FIG. 1 is a top view showing an overall configuration of the embodiment of the automatic analysis device of the present invention; FIG. 2 is a flowchart showing a treatment procedure of determining recommendation of periodic cleaning maintenance in the embodiment of the automatic analysis device of the present invention; FIG. 3 is a flowchart showing a treatment procedure of determining recommendation of periodic replacement maintenance in the embodiment of the automatic analysis device of the present invention; FIG. 4 is a passage view of a detection system passage; and FIG. 5 is a passage view of a B/F separation passage.

In FIG. 1, an immunoanalysis device 100 is configured to have a control device 101, a rack 102, a rack conveyance line 104, a sample dispensing nozzle 105, an incubator disk 106, a conveyance mechanism 108, a holding member 109, a reaction container agitation mechanism 110, a disposal hole 111, a reagent disk 113, a reagent dispensing nozzle 117, a B/F separation conveyance mechanism 118, a B/F separation mechanism 119, a reaction liquid suction nozzle 120 for B/F separation, a buffer solution discharge nozzle 121, an agitation mechanism 122 after B/F separation, a reaction liquid suction nozzle 123 for detection, a detection unit 124, and the like.

In the immunoanalysis device 100, a sample container 103 which holds a sample (specimen) is provided in the rack 102. In addition, the rack conveyance line 104 moves the sample container 103 which is provided in the rack 102 to a sample dispensing position in the vicinity of the sample dispensing nozzle 105.

The sample dispensing nozzle 105 is capable of performing a rotary operation and a vertical operation. The sample dispensing nozzle 105 sucks a sample held by the sample container 103 and discharges the sucked sample to a reaction container 107 on the incubator disk 106.

The incubator disk 106 is configured such that a plurality of reaction containers 107 can be installed therein. The incubator disk 106 performs a rotation operation in which the reaction containers 107 installed in a circumferential direction are moved to predetermined positions such as a reaction container installation position, a reagent discharge position, a sample discharge position, a detection position, and a reaction container disposal position.

The conveyance mechanism 108 is movable in three directions including an X axis, a Y axis, and a Z axis. The conveyance mechanism moves within a range of predetermined places such as the holding member 109, the reaction container agitation mechanism 110, the disposal hole 111, a chip installation position 112 of a sample dispensing chip, and the incubator disk 106, and conveys the sample dispensing chip or the reaction container 107.

A plurality of reaction containers 107 and a plurality of sample dispensing chips to be used are installed in the holding member 109.

The reaction container agitation mechanism 110 is a mechanism for agitation which mixes a sample and a reagent in the reaction container 107 by adding a rotating motion to the reaction container 107.

The disposal hole 111 is a hole for disposing used sample dispensing chips or reaction container 107.

A plurality of reagent containers 114 which hold a reagent are installed in the reagent disk 113. The inside of the reagent disk 113 maintains a predetermined temperature, and a cover 115 is provided above the reagent disk 113. A cover opening 116 is provided in a part of the cover 115.

The reagent dispensing nozzle 117 is rotatable and vertically movable. The reagent dispensing nozzle is configured so as to suck a reagent which is held by the reagent container 114 in the reagent disk 113 and discharge the sucked reagent to the reaction container 107 on the incubator disk 106.

The B/F separation conveyance mechanism 118 moves a reaction container 107, which has been on the incubator disk 106 for a predetermined amount of time, to a reaction container conveyance position.

The B/F separation mechanism (treatment mechanism) 119 is a mechanism which separates magnetic particles from a reaction liquid which does not contain magnetic particles by magnetically attracting the magnetic particles, which contain a substance immunologically bonding to a measurement object existing in the reaction liquid in the reaction container 107 that is conveyed to the reaction container conveyance position by the B/F separation conveyance mechanism 118, to an inner wall of the reaction container 107.

The reaction liquid suction nozzle 120 for B/F separation is configured so as to be rotatable and vertically movable and sucks a reaction liquid which does not contain magnetic particles in the reaction container 107 by being moved above the reaction container 107, which has been on the B/F separation mechanism 119 for a predetermined amount of time, to be lowered.

The buffer solution discharge nozzle 121 is configured so as to be rotatable and vertically movable and discharges a buffer solution to the reaction container 107 by being moved above the reaction container 107, from which the reaction liquid that does not contain magnetic particles is sucked, to be lowered, on the B/F separation mechanism 119.

The agitation mechanism 122 after B/F separation mixes the buffer solution and the magnetic particles in the reaction container by adding a rotating motion to the reaction container 107. The reaction container 107 after the mixing is conveyed to a B/F separation end position of the incubator disk 106 by the B/F separation conveyance mechanism 118.

The reaction liquid suction nozzle 123 for detection is rotatable and vertically movable, and is a nozzle for feeding a reaction liquid in the reaction container 107 on the incubator disk 106 to the detection unit 124 by sucking the reaction liquid.

The detection unit (measurement unit) 124 detects a concentration or the like of a detection object in the reaction liquid which has been sucked from or fed by the reaction liquid suction nozzle 123 for detection.

The control device 101 is schematically provided with a storage unit 101a, an arithmetic unit 101b, and a determination unit 101c. This control device 101 creates a plan for analysis based on a measurement request from an operator; and controls an initial preparation operation, which is performed before analysis processing, a dispensing operation of each portion, and an operation, such as analysis processing of a detection result of the detection unit 124, of mechanisms including the immunoanalysis device 100 and a biochemical analysis device 200 based on this plan; to perform analysis.

In addition, the control device 101 determines whether it is necessary to perform maintenance (periodic cleaning or periodic replacement) on a B/F separation passage of the reaction liquid suction nozzle 120 for B/F separation or the like and a detection passage of the reaction liquid suction nozzle 123 for detection, the detection unit 124, and the like, based on the properties of a solution such as a specimen, a reagent, and a reaction liquid which is obtained by reacting the specimen and the reagent, an analysis protocol which defines treatment conditions (pretreatment before analysis, solution feeding conditions, dispensing conditions, or the like) of these solutions, the number of times of dispensing a solution, the number of times of feeding a solution, and the number of times of measurement.

The storage unit 101a of the control device 101 stores the properties of a solution and the analysis protocol. The properties of a solution include information relating to a specimen; information relating to a reagent; information relating to a reaction liquid which is obtained by reacting the specimen and the reagent; and information about the concentration of a biological component which is measured by the detection unit 124. In addition, the analysis protocol includes information relating to conditions of treatment which is performed on a specimen, a reagent, and a reaction liquid, for example, the presence/absence of a B/F separation treatment in the B/F separation mechanism 119. Furthermore, the properties of a solution and the analysis protocol include information about a plurality of factors (for example, passage load) relating to maintenance of the B/F separation passage and the detection passage. Main factors for the passage load include the type of sample, the amount of a sample, and components of a sample. In addition, main factors for the passage load in the analysis protocol include the presence/absence of a B/F separation process before detection.

In addition, the storage unit 101a stores a weighting coefficient which is obtained by quantifying an influence of each factor with respect to the above-described plurality of factors or arithmetic results of the total amount of a load in the arithmetic unit 101b. For example, the presence/absence of the B/F separation process before detection is defined by the analysis protocol of each measurement, and therefore, it is possible to define the weighting coefficient of the passage load in accordance with the analysis protocol.

The arithmetic unit 101b calculates a total amount (Wbft, Wdt, Wmt) of a load with respect to the B/F separation passage, the detection passage, and the detection unit based on the weighting coefficient, the number of times of dispensing, feeding, and measuring the solutions, which are stored in the storage unit 101a. The total amount of the load is output to and stored in the storage unit 101a.

The determination unit 101c determines whether it is necessary to perform maintenance (periodic cleaning or periodic replacement) on the B/F separation passage and the detection passage, by comparing a threshold value (Lbf, Ld, Lm) with the total amount of the load calculated by the arithmetic unit 101b, and outputs a display signal for display to a display unit such as a display 130.

In addition, the determination unit 101c predicts a timing when the total amount of a load reaches a threshold value, from the transition of the total amount of a load which has been stored in the storage unit 101a, and outputs the measurement result to the display 130.

The display 130 inputs a signal of an analysis result of a specimen calculated by the control device 101 and displays the result. In addition, the display 130 displays whether maintenance of the B/F separation passage and the detection passage is required which is determined by the control device 101. Furthermore, the display 130 displays a predicted timing for maintenance.

Next, the above-described operation in the embodiment of the automatic analysis device of the present invention will be described.

The control device 101 receives a measurement input signal from an operator and outputs a control signal to each mechanism in a device for performing analysis to control the operation.

First, the conveyance mechanism 108 moves above the holding member 109 to be lowered, and holds an unused reaction container 107 to be elevated. Then, the conveyance mechanism 108 moves above a reaction container installation position of the incubator disk 106 to be lowered, and installs the unused reaction container 107 on the incubator disk 106.

In addition, the conveyance mechanism 108 moves above the holding member 109 to be lowered, and holds an unused sample dispensing chip to be elevated. Then, the conveyance mechanism 108 moves above the chip installation position 112 to be lowered, and installs the unused sample dispensing chip on the chip installation position 112. Then, the sample dispensing nozzle 105 moves above the chip installation position 112 to be lowered, and installs the sample dispensing chip at a tip end of the sample dispensing nozzle 105.

The reagent dispensing nozzle 117 is rotationally moved above the opening 116 of the reagent disk cover 115 to be lowered, and brings a tip end of the reagent dispensing nozzle 117 into contact with a reagent in a predetermined reagent container to suck a predetermined amount of the reagent. Next, the reagent dispensing nozzle 117 moves above a reagent discharge position of the incubator disk 106 and discharges the reagent to the reaction container 107 installed on the incubator disk 106.

In addition, the sample dispensing nozzle 105 installed with a sample dispensing chip moves above the sample container 103, which is placed in the rack 102, to be lowered, and sucks a predetermined amount of a sample held by the sample container 103. Then, the sample dispensing nozzle 105 which has sucked the sample moves to a sample discharge position of the incubator disk 106 to be lowered, and discharges the sample to the reaction container 107 to which a reagent is dispensed and which is on the incubator disk 106. After the discharge of the sample, the sample dispensing nozzle 105 moves above the disposal hole 111 to dispose of the used sample dispensing chip through the disposal hole 111.

Then, the control device 101 moves the reaction container 107, to which the sample and the reagent are discharged, to a reaction container conveyance position by rotating the incubator disk 106, and conveys the reaction container 107 to the reaction container agitation mechanism 110 using the conveyance mechanism 108.

The reaction container agitation mechanism 110 adds a rotating motion to the reaction container 107 and stirs the sample and the reagent so as to mix them in the reaction container 107. Then, the control device 101 returns the reaction container 107, which has been stirred, to the reaction container conveyance position of the incubator disk 106 using the conveyance mechanism 108.

Next, the control device 101 selectively performs the following B/F separation process in accordance with the analysis protocol.

First, a reaction container 107, which has been on the incubator disk 106 for a predetermined amount of time, moves to the reaction container conveyance position through rotation of the incubator disk 106 and conveys the reaction container to the B/F separation mechanism 119 using the B/F separation conveyance mechanism 118.

Next, magnetic particles, which contain a substance immunologically bonding to a measurement object existing in the reaction liquid in the reaction container 107, are magnetically attracted to an inner wall of the reaction container 107 by the B/F separation mechanism 119; the reaction liquid suction nozzle 120 for B/F separation is moved above the reaction container 107, which has been on the B/F separation mechanism 119 for a predetermined amount of time, to be lowered; and the reaction liquid which does not contain magnetic particles in the reaction container 107 is sucked.

Next, the buffer solution discharge nozzle 121 is moved above the reaction container 107, in which the reaction liquid containing no magnetic particles is sucked on the B/F separation mechanism 119, to be lowered; a buffer solution is discharged into the reaction container 107, which is then conveyed to the agitation mechanism 122 after B/F separation by the B/F separation conveyance mechanism 118.

Then, a rotating motion is added to the reaction container 107 in the agitation mechanism 122 after B/F separation to mix the buffer solution with the magnetic particles in the reaction container. The reaction container 107 which has been stirred is returned to a B/F separation end position of the incubator disk 106 by the agitation mechanism 122 after B/F separation.

Next, a detection process that detects a measurement object in a reaction liquid is performed.

First, the reaction liquid suction nozzle 123 for detection is moved above a reaction container 107, to which the sample and the reagent are dispensed and which has been on the incubator disk 106 for a predetermined amount of time, or a reaction container 107, which has been subjected to B/F separation, to be lowered, and then, a reaction liquid in the reaction container 107 is sucked. The reaction liquid is fed to a flow cell type detection unit 124 through a liquid feeding passage 124a and a measurement object is detected in the detection unit 124.

The control device 101 derives measurement results (such as concentration of a detection object in a sample) based on detected values of the measurement object, which has been detected by the detection unit 124, and displays the measurement results using the display 130 or the like.

In addition, the control device 101 moves the reaction container 107, from which the reaction liquid is sucked, to a reaction container disposal position through rotation of the incubator disk 106; moves the reaction container above a disposal hole 111a from the incubator disk 106 using the conveyance mechanism 108; and disposes of the reaction container through the disposal hole 111a.

Analysis using a biochemical analysis device 200 is selectively performed in accordance with an analysis request item.

First, the rack 102 that holds a sample container 103 to which a sample has been dispensed in the immunoanalysis device 100 is transferred to the biochemical analysis device 200 using a rack conveyance line 125 between analysis devices and analysis using the biochemical analysis device 200 is performed.

The control device 101 displays measurement results on the display 130 or the like based on detected values of a measurement object in the biochemical analysis device 200.

Next, a method of determining a timing for periodic cleaning and periodic replacement of the B/F separation passage of the reaction liquid suction nozzle 120 for B/F separation or the like, or the detection passage of the reaction liquid suction nozzle 123 for detection, the detection unit 124, and the like, the method being performed in the control device of the present embodiment of the automatic analysis device will be described below using FIGS. 2 and 3.

First, one example of a processing flow up to a recommendation of periodic cleaning maintenance of a passage will be described using FIG. 2.

First, the arithmetic unit 101b of the control device 101 starts a K-th measurement from an arbitrary starting point which becomes Kd-th after periodic cleaning maintenance of the detection passage is performed or Kbf-th after periodic cleaning maintenance of the B/F separation passage is performed (Step S201).

Next, the arithmetic unit 101b of the control device 101 calls a weighting coefficient $S1k$ of a specimen, which is used in the K-th measurement, with respect to each passage load in accordance with information about the type of sample stored in the storage unit 101a of the control device 101 and performs determination (Step S202).

As a factor for a flow rate load in relation to the type of sample, for example, whole blood which contains a blood corpuscle component generally has a passage load greater than that of serum or plasma. In addition, in general, the greater a factor for a flow rate load in relation to the amount of a sample, the larger the passage load. The type of sample and the amount of a sample are defined by the analysis protocol of each measurement, and therefore, it is possible to define the weighting coefficient of the passage load in accordance with the analysis protocol.

For example, as the weighting coefficient based on the type of sample, a serum sample is set to 1, a urine sample is set to 1, a whole blood sample is set to 3, other samples are set to 1, and a case where there is no information is set to 1.

Next, the arithmetic unit 101b of the control device 101 calls a weighting coefficient $S2k$ of a specimen, which has been measured in the K-th measurement, with respect to each passage load in accordance with information about components of the sample stored in the storage unit 101a of the control device 101 and performs determination (Step S203).

As a factor for a flow rate load in relation to the components of the sample, for example, in general, the greater the amount of protein (total protein, albumin, or the like) or lipid (total cholesterol, neutral fat, or the like), the larger the passage load. In some cases, as the content of protein or lipid, after an immune item is measured by the immunoanalysis device 100, a biochemical item of the same sample is measured by the biochemical analysis device 200. In this case, it is possible to define the weighting coefficient in relation to the passage load of the immunoanalysis device 100 in accordance with the measured value of the biochemical item which is input from the biochemical analysis device 200 to the control device 101.

For example, as the weighting coefficient based on the components of the sample, a normal sample is set to 1, a high protein-containing sample is set to 2, a high lipid-containing sample is set to 3, a hemolysis sample is set to 2, and a case where there is no information is set to 1. However, in a case where it is impossible to obtain a measured value in relation to the components of the sample, it is desirable not to apply such a weighting coefficient.

Next, the arithmetic unit 101b of the control device 101 calls a weighting coefficient R1k of a reagent, which has been used in the K-th measurement, with respect to each passage load in accordance with information about components based on a reagent item stored in the storage unit 101a of the control device 101 and performs determination (Step S203').

Examples of a factor for flow rate load in relation to the components of the reagent include a reductant (DTT or melcaptoethanol) or the like as a protein modifying agent.

For example, as the weighting coefficient based on the components of the reagent, a normal sample is set to 1 and a reductant-containing reagent is set to 2.

Next, the arithmetic unit 101b of the control device 101 determines whether a B/F separation process before detection has been performed in the K-th measurement based on information about the analysis protocol stored in the storage unit 101a of the control device 101 (Step S204). Accordingly, the detection passage load amount Wdk and the B/F separation passage load amount Wbfk depending on whether the B/F separation process before detection is performed are calculated.

When it is determined that there is no B/F separation process before detection in Step S204, the reaction liquid is not sucked by the reaction liquid suction nozzle 120 for B/F separation. Therefore, the weighting coefficient of the passage load with respect to the B/F separation passage becomes zero and a weighting coefficient in relation to the above-described components of the sample is applied to the passage load with respect to the detection passage.

Accordingly, the arithmetic unit 101b of the control device 101 sets the detection passage load amount Wdk to a sum (Wdk=S1k+S2k+R1k) of the coefficients S1k and S2k based on the type and the components of the sample and the weighting coefficient R1k based on the reagent (Step S205).

In addition, the arithmetic unit 101b of the control device 101 sets the B/F separation passage load amount Wbfk of the B/F separation passage without contamination load to 0 (Wbfk=0) (Step S206).

In contrast, when it is determined that there is a B/F separation process before detection, the reaction liquid is sucked by the reaction liquid suction nozzle 120 for B/F separation. Therefore, the weighting coefficient in relation to the above-described components of the sample is applied to the passage load with respect to the B/F separation passage and the weighting coefficient based on the passage load of the buffer solution which has been replaced in the B/F separation passage is applied to the passage load with respect to the detection passage. This is because the buffer solution does not contain protein or lipid derived from the sample, and therefore, the passage load is smaller than that of the sample.

Accordingly, the arithmetic unit 101b of the control device 101 sets the detection passage load amount Wdk resulting from a replaced solution after B/F separation to, for example, 0.5 (Wdk=0.5) (Step S207).

In addition, the arithmetic unit 101b of the control device 101 sets the B/F separation passage load amount Wbfk to a sum (Wbfk=S1k+S2k+R1k) of the coefficients S1k and S2k based on the type and the components of the sample and the weighting coefficient R1k based on the reagent (Step S208).

Next, the arithmetic unit 101b of the control device 101 calculates a sum (total detection passage load amount Wdt) of the amounts of loads with respect to the detection passage from a first measurement to a Kd-th measurement after periodic cleaning maintenance of the detection passage is performed, using the following Formula (1) (Step S209).

$$Wdt = \sum_{i=1}^{kd} Wdi \qquad (1)$$

Next, the determination unit 101c of the control device 101 determines whether the total detection passage load amount Wdt which has been calculated in Step S209 exceeds a predetermined threshold value Ld which has been previously defined (Step S210). Here, the threshold value Ld of the total detection passage load amount Wdt is set to, for example, 4000.

When it is determined that the total detection passage load value Wdt does not exceed the threshold value Ld in Step S210, the process proceeds to Step S214.

In contrast, when it is determined that the total detection passage load value Wdt exceeds the threshold value Ld in Step S210, the determination unit 101c of the control device 101 outputs a caution signal, which urges a user to perform periodic cleaning maintenance of the detection passage, to the display 130 and displays the signal on the display 130 (Step S211). For example, a sentence such as "please perform periodic cleaning maintenance of the detection passage" is highlighted and displayed on the display 130, but the present invention is not limited thereto.

When the time reaches a periodic cleaning timing, a user performs a periodic cleaning process of the detection passage by operating the control device 101 or automatically performs a periodic cleaning process of the detection passage by controlling the control device 101.

The cleaning process of the detection passage will be described using FIG. 4.

In periodic cleaning of a detection passage 400, the reaction liquid suction nozzle 123 for detection is moved above a cleaning container 127 for a reaction liquid suction nozzle for detection, which is installed near the detection unit 124, to be lowered, and then, a passage switching valve 404 is open. In contrast, a reaction liquid suction syringe 405 is driven to a suction side in a state where a passage switching valve 407 is closed, and a cleaning liquid 401 in the cleaning container 127 for reaction liquid suction nozzle for detection is sucked. The sucked cleaning liquid is held in a passage 402 and a passage 403 which include the reaction liquid suction nozzle 123 for detection and the detection unit 124 for a certain amount of time, and then, the passage switching valve 404 is closed. In contrast, the reaction liquid suction syringe 405 is driven to a discharge side in a state where the passage switching valve 407 is open, and the cleaning liquid is sent to a waste liquid passage 408.

The cleaning liquid 401 contains, for example, a surfactant, hypochlorous acid, or the like, and therefore, it is possible to efficiently remove protein or lipid in the passage.

Next, the determination unit 101c of the control device 101 determines whether periodic cleaning maintenance of the detection passage has been performed by a user (Step S212).

When it is determined that periodic cleaning maintenance has been performed in Step S212, the determination unit 101c of the control device 101 resets Kd, which indicates a count of the number of times of measurement after the above-described periodic cleaning maintenance of the detection passage is performed, to 0 (Step S213). Then, the process proceeds to Step S214.

In contrast, when it is determined that periodic cleaning maintenance has not been performed in Step S212, the determination unit 101c of the control device 101 advances the process to Step S214 without resetting the above-described Kd to 0.

In addition, the determination unit 101c of the control device 101 calculates a sum (total B/F separation passage load amount Wbft) of the amounts of loads with respect to the B/F separation passage from a first measurement to a Kbf-th measurement after periodic cleaning maintenance of the B/F separation passage is performed, using the following Formula (2) (Step S214).

$$Wbft = \sum_{i=1}^{kbf} Wbfi \quad (2)$$

Next, the determination unit 101c of the control device 101 determines whether the total B/F separation passage load amount Wbft calculated in Step S214 exceeds a predetermined threshold value Lbf which has been previously defined (Step S215). Here, the threshold value Lbf of the B/F separation passage load amount is set to, for example, 8000.

When it is determined that the total B/F separation passage load amount Wbft does not exceed the threshold value Ldf in Step S215, the arithmetic unit 101b of the control device 101 starts the K+1-th measurement from an arbitrary starting point (Step S219).

In contrast, when it is determined that the total B/F separation passage load amount Wbft exceeds the threshold value Lbf in Step S215, the determination unit 101c of the control device 101 outputs a caution signal, which urges a user to perform periodic cleaning maintenance of the B/F separation passage, to the display 130 and displays the signal on the display 130 (Step S216). For example, a sentence such as "please perform periodic cleaning maintenance of the B/F separation passage" is highlighted and displayed on the display 130.

When the time reaches a periodic cleaning timing, a user performs a periodic cleaning process of the B/F separation passage by operating the control device 101 or automatically performs a periodic cleaning process of the B/F separation passage by controlling the control device 101.

The cleaning process of the B/F separation passage will be described using FIG. 5.

In periodic cleaning of a B/F separation passage 500, the reaction liquid suction nozzle 120 for B/F separation is moved above a cleaning container 126 for a reaction liquid suction nozzle for B/F separation, which is installed near the B/F separation mechanism 119, to be lowered, and then, a passage switching valve 503 is open. In contrast, a reaction liquid suction syringe 504 for B/F separation is driven to a suction side in a state where a passage switching valve 506 is closed, and a cleaning liquid 501 in the cleaning container 126 for a reaction liquid suction nozzle for B/F separation is sucked. The cleaning liquid is held in a passage 502 which includes the reaction liquid suction nozzle 120 for B/F separation for a certain amount of time, and then, the passage switching valve 503 is closed. In contrast, the reaction liquid suction syringe 504 for B/F separation is driven to a discharge side in a state where the passage switching valve 506 is open, and the cleaning liquid is sent to a waste liquid passage 507.

The cleaning liquid 501 contains, for example, a surfactant, hypochlorous acid, or the like, and therefore, it is possible to efficiently remove protein or lipid in the passage.

Next, the determination unit 101c of the control device 101 determines whether periodic cleaning maintenance of the B/F separation passage has been performed by a user (Step S217).

When it is determined that periodic cleaning maintenance has been performed in Step S217, the determination unit 101c of the control device 101 resets Kbf, which indicates a count of the number of times of measurement after the above-described periodical cleaning maintenance of the B/F separation passage is performed, to 0 (Step S218). Then, the arithmetic unit 101b of the control device 101 starts the K+1-th measurement from an arbitrary starting point (Step S219).

In contrast, when it is determined that periodic cleaning maintenance has not been performed in Step S217, the determination unit 101c of the control device 101 does not reset the above-described Kbf to 0 and the arithmetic unit 101b starts the K+1-th measurement from an arbitrary starting point (Step S219).

In a case where it is expected that there is less variation in components contained in a reagent or the properties of the reagent to be used in measurement, the weighting coefficient R1$k$ based on the type of reagent may be fixed. In addition, even in a case where it is clear whether a whole blood sample is not measured, the weighting coefficient based on the type of sample may be fixed. Furthermore, the proportion of components of the sample is unknown during initial measurement, and therefore, the weighting coefficient based on the components of the sample is also fixed. In the above-described case, for example, S1$k$=0.5, S2$k$=0.5, Wdk=1.0, and Wbfk=1.0 are set.

In addition, in the present Example, the threshold values Ld and Lbf for determining whether periodic cleaning maintenance of a passage is recommended are set to, for example, Ld=4000 and Lbf=8000. However, the present invention is not limited to these values and appropriate changes can be made in accordance with the condition or the like of the device.

Next, one example of a processing flow up to a recommendation of periodic replacement maintenance of the detection unit 124 in a detection passage, the processing being performed in the control device of the present embodiment of the automatic analysis device will be described below using FIG. 3.

First, the arithmetic unit 101b of the control device 101 starts a K-th measurement from an arbitrary starting point which becomes Km-th after periodic replacement maintenance of the detection unit 124 is performed (Step S301).

Next, the arithmetic unit 101b of the control device 101 determines a weighting coefficient S1$k$ of a specimen, which is used in the K-th measurement, with respect to each passage load in accordance with information about the type of sample stored in the storage unit 101a of the control device 101 (Step S302).

Next, the arithmetic unit 101b of the control device 101 determines a weighting coefficient S2k of a specimen, which has been measured in the K-th measurement, with respect to each passage load in accordance with information about the components of the sample stored in the storage unit 101a of the control device 101 (Step S303).

Next, the arithmetic unit 101b of the control device 101 calls a weighting coefficient R1k of a reagent, which has been used in the K-th measurement, with respect to each passage load in accordance with information about components based on a reagent item stored in the storage unit 101a of the control device 101 and performs determination (Step S303′).

Next, the arithmetic unit 101b of the control device 101 determines whether a B/F separation process before detection has been performed in the K-th measurement based on information about the analysis protocol stored in the storage unit 101a of the control device 101 (Step S304).

When it is determined that there is no B/F separation process before detection in Step S304, the arithmetic unit 101b of the control device 101 sets the detection unit load amount Wmk to a sum (Wmk=S1k+S2k+R1k) of the coefficients S1k and S2k based on the type and the components of the sample and the weighting coefficient R1k based on the reagent (Step S305).

In contrast, when it is determined that there is a B/F separation process before detection, the arithmetic unit 101b of the control device 101 sets the detection unit load amount Wmk to, for example, 0.5 (Wdk=0.5) (Step S306).

Next, the arithmetic unit 101b of the control device 101 calculates a sum (total detection unit load amount Wmt) of the amounts of loads with respect to the detection unit 124 from a first measurement to a Km-th measurement after periodic replacement maintenance of the detection unit is performed, using the following Formula (3) (Step S307).

$$Wmt = \sum_{i=1}^{km} Wmi \quad (3)$$

Next, the determination unit 101c of the control device 101 determines whether the total detection unit load amount Wmt which has been calculated in Step S307 exceeds a predetermined threshold value Lm which has been previously defined (Step S308). Here, the threshold value Lm of the total detection unit load amount Wmt is set to, for example, 100000.

When it is determined that the total detection unit load amount Wmt does not exceed the threshold value Lm in Step S308, the arithmetic unit 101b of the control device 101 starts the K+1-th measurement from an arbitrary starting point (Step S312).

In contrast, when it is determined that the total detection unit load amount Wmt exceeds the threshold value Lm in Step S308, the determination unit 101c of the control device 101 displays a caution, which urges a user to perform periodic replacement maintenance of the detection unit 124, on the display 130 (Step S309). For example, a sentence such as "please perform periodic replacement maintenance of the detection unit" is highlighted and displayed on the display 130.

When the time reaches a periodic replacement timing, a user performs replacement preparation by operating the control device 101 and performs a replacement operation.

Next, the determination unit 101c of the control device 101 determines whether periodic replacement maintenance of the detection unit 124 has been performed by a user (Step S310).

When it is determined that periodic replacement maintenance has been performed in Step S310, the determination unit 101c of the control device 101 resets Km, which indicates a count of the number of times of measurement after the above-described periodic replacement maintenance of the detection unit 124 is performed, to 0 (Step S311). Then, the arithmetic unit 101b of the control device 101 starts the K+1-th measurement from an arbitrary starting point (Step S312).

In contrast, when it is determined that periodic replacement maintenance has not been performed in Step S310, the determination unit 101c of the control device 101 does not reset the above-described Km to 0 and the arithmetic unit 101b starts the K+1-th measurement from an arbitrary starting point (Step S312).

Similarly to the description of FIG. 2, in a case where it is expected that there is less variation in components contained in a reagent or the properties of the reagent to be used in measurement, the weighting coefficient R1k based on the type of reagent may be fixed. In addition, even in a case where it is clear whether a whole blood sample is not measured, the weighting coefficient Sk1 based on the type of sample may be fixed. Furthermore, the proportion of components of the sample is unknown during initial measurement, and therefore, the weighting coefficient S2k based on the components of the sample is also fixed. In the above-described case, for example, S1k=0.5, S2k=0.5, and Wmk=1.0 are set.

In addition, in this flowchart, the threshold value Lm for determining whether periodical cleaning maintenance of a passage is recommended is set to, for example, Lm=10000. However, the present invention is not limited to this value and appropriate changes can be made in accordance with the condition or the like of the device.

It is determined whether it is necessary to perform periodic cleaning and periodic replacement on the B/F separation passage of the reaction liquid suction nozzle 120 for B/F separation or the like, or the detection passage of the reaction liquid suction nozzle 123 for detection, the detection unit 124, and the like, in accordance with the above-described treatment procedures and recommendation of periodic cleaning or periodic replacement is displayed on the display 130. Accordingly, information about periodic cleaning or periodic replacement is provided to an operator and appropriate maintenance is performed.

In addition, it is possible to predict the timing for periodic cleaning or periodic replacement from the transition of the total value of the passage load values of each passage, to obtain the timing for recommending periodic cleaning or periodic replacement in advance using the control device 101, and to display the obtained time on the display 130.

For example, the number of times of measurement is given on a lateral axis and the total value of the passage load values is given on a longitudinal axis and an approximate expression at this time is calculated to obtain the number of times of measurement at which the total value of the passage load values calculated using the approximate expression exceeds a predetermined threshold value. A timing for periodic cleaning or a timing for periodic replacement is displayed from the obtained number of times of measurement.

In the above-described embodiment of the automatic analysis device of the present invention, it is determined whether the device is in a state where it is necessary to perform periodic cleaning or periodic replacement on the B/F separation passage of reaction liquid suction nozzle 120 for B/F separation or the like and the detection passage of the reaction liquid suction nozzle 123 for detection, the detection unit 124, and the like, based on the properties of a specimen, a reagent, and a reaction liquid which is obtained by reacting the specimen and the reagent, an analysis protocol which defines treatment conditions of these solutions, and the number of times of dispensing, feeding, and measuring the solutions; and the determined result is output as a display signal to the display 130.

Accordingly, it is possible to provide an operator with information about an adequate timing for periodic cleaning or periodic replacement in accordance with analysis conditions since the timing for maintenance of the nozzles, the passages, and the detection unit, which are provided in an immunoanalysis device, is defined based on the properties of the specimen or the reaction liquid in each measurement, and the analysis protocol as well as the number of times of measurement. Accordingly, it is possible to perform adequate periodic cleaning or periodic replacement in accordance with various analysis conditions, and therefore, the frequency of periodic cleaning or periodic replacement does not become too frequent or too infrequent, thereby realizing improvement in usability and securing analysis performance.

In addition, the control device 101 has the storage unit 101a which stores a weighting coefficient which is obtained by quantifying an influence of each factor with respect to the properties of the solutions and the analysis protocol including information about a plurality of factors relating to maintenance of the B/F separation passage and the detection passage, and a plurality of factors; the arithmetic unit 101b which calculates a total amount (Wbft, Wdt, Wmt) of a load with respect to the B/F separation passage, the detection passage, the detection unit based on the weighting coefficient and the number of times of dispensing, feeding, and measuring the solutions; and the determination unit 101c which determines whether it is necessary to perform periodic cleaning or periodic replacement of the B/F separation passage and the detection passage by comparing a threshold value (Lbf, Ld, Lm) and the calculated total amount of the load. Accordingly, it is possible to accurately define the frequency of maintenance of the nozzle, the passage, and the detection unit based on the property of a specimen or an analysis protocol in each measurement, and therefore, it is possible to more accurately provide an operator with adequate information about the timing for periodic cleaning or periodic replacement corresponding to measurement conditions in accordance with analysis conditions.

Furthermore, the control device 101 performs control so as to store the total amount of a load calculated by the arithmetic unit 101b, in the storage unit 101a and to display a timing when the total amount of a load reaches a threshold value on the display 130, from the transition of the total amount of a load, the timing being predicted by the determination unit 101c. Accordingly, it is possible to provide an operator with adequate information about a timing for periodic cleaning and periodic replacement in advance, and therefore, it is possible to efficiently perform preparation provided for periodic cleaning and periodic replacement. Accordingly, it is possible to further suppress omission of periodic cleaning or the like, and therefore, it is possible to achieve more improved usability and analysis performance.

In addition, the device further includes the B/F separation mechanism 119 which separates the component of a specimen and a reagent from a reaction liquid. The control device 101 recognizes the presence/absence of a separation treatment in the B/F separation mechanism 119 based on the analysis protocol to use the recognized information in determining the necessity of maintenance. Accordingly, it is possible to provide adequate information of periodic cleaning or periodic replacement more in accordance with actual analysis conditions.

The device further includes the detection unit 124 which measures the concentration of a biological component included in the specimen. Similarly, it is also possible to provide adequate information of periodic cleaning or periodic replacement more in accordance with actual analysis conditions through the control device 101 determining the properties of the solutions based on the concentration of the biological component measured by the detection unit 124.

The automatic analysis device of the present invention is not limited to the above-described embodiment and various modifications and applications can be made.

For example, the B/F separation passage and the detection passage have been described as examples of the members which determine the necessity of maintenance. However, the members are not limited thereto and examples thereof include a member which comes into contact with at least any one of solutions including a specimen, a reagent, and a reaction liquid which is obtained by reacting the specimen and the reagent. Examples thereof include a specimen dispensing passage, a reagent dispensing passage, or the like which is a passage for dispensing or feeding a solution.

Furthermore, in the above-described embodiment, the immunoanalysis device has been exemplified as the automatic analysis device, but the automatic analysis device is not limited thereto. For example, it is also possible to apply the present invention to the biochemical analysis device 200. Examples of the member in the biochemical analysis device 200 include a mechanism relating to dispensing a specimen (specimen dispensing nozzle or the like).

In addition, other examples of the member include a specimen suction passage for electrolyte analysis and an electrolyte measurement unit which is provided as a part of this passage.

In addition, in the above-described embodiment, it is set such that it is possible to perform a next measurement (K+1-th) even in a case where the total amount of a load of passages exceeds a threshold value. It is also possible to change a caution level which urges a user to perform maintenance in accordance with the balance or the excessive amount of the total amount of a load of passages with respect to the threshold value and display the caution level on an operation screen or to provide a caution flag to a measurement result when the total amount of a load of passages exceeds the threshold value. Accordingly, it is possible to achieve more improved reliability of the analysis result.

In addition, it is also possible to include a function of automatically performing maintenance using the device in a case where the total amount of a load of passages exceeds the threshold value. Accordingly, it is possible to achieve improvement in usability of the device.

REFERENCE SIGNS LIST 100 immunoanalysis device,
101 control device, 101a storage unit,
101b arithmetic unit,
101c determination unit,
102 rack,
103 sample container,
104 rack conveyance line,
105 sample dispensing nozzle,
106 incubator disk,
107 reaction container,
108 conveyance mechanism,
109 holding member,
110 reaction container agitation mechanism
111, 111a disposal hole,
112 chip installation position,
113 reagent disk,
114 reagent container,
115 reagent disk cover,
116 reagent disk cover opening,
117 reagent dispensing nozzle,
118 B/F separation conveyance mechanism,
119 B/F separation mechanism,
120 reaction liquid suction nozzle for B/F separation,
121 buffer solution discharge nozzle,
122 agitation mechanism after B/F separation,
123 reaction liquid suction nozzle for detection,
124 detection unit,
124a liquid feeding passage,
125 rack conveyance line between analysis devices,
126 cleaning container for reaction liquid suction nozzle for B/F separation,
127 cleaning container for reaction liquid suction nozzle for detection,
130 display,
200 biochemical analysis device,
400 detection passage,
401 cleaning liquid for reaction liquid suction nozzle for detection
402 nozzle-side passage,
403 detection unit-side passage,
404 detection unit-side passage switching valve,
405 reaction liquid suction syringe for detection,
407 drain-side passage switching valve,
408 drain passage,
500 B/F separation passage,
501 B/F separation reaction liquid suction nozzle-cleaning liquid,
502 nozzle-side passage,
503 nozzle-side passage switching valve,
504 reaction liquid suction syringe for B/F separation,
506 drain-side passage switching valve,
507 drain passage.

The invention claimed is:

1. An automatic analysis device which measures a specimen, comprising:
a B/F separation mechanism that performs a B/F separation process in which a reacted component and an unreacted component are separated from a liquid having the specimen and the reagent reacted with each other;
a detection unit that detects the reacted component in the liquid subjected to the B/F separation process;
a member which supplies at least one of the specimen, the reagent, and the liquid to the B/F separation mechanism or the detection unit, and which comes into contact with the at least one of the specimen, the reagent, and the liquid; and
a control device configured to include:
an arithmetic unit that calculates a respective load applied to the member upon performing each of a plurality of analysis protocols, including an analysis protocol of the specimen, in accordance with the B/F separation process being included in the analysis protocol of the specimen and in accordance with properties of the specimen and the reagent in the analysis protocol of the specimen, and calculates a total load applied to the member from the respective load of each of the plurality of analysis protocols, and
a determination unit that determines when to perform maintenance of the member in accordance with the total load calculated by the arithmetic unit for the analysis protocols,
wherein the control device is further configured to output a display signal indicating to perform the maintenance of the member according to the determination result by the determination unit.

2. The automatic analysis device according to claim 1, further comprising:
a display unit that displays a message to prompt a user to perform the maintenance of the member as the display signal,
wherein the control device is further configured to include a storage unit that stores the total load,
wherein the determination unit predicts a timing when the total load exceeds a threshold value on the basis of a transition of the total load which has been stored in the storage unit, and
wherein the control device is further configured to output to the display unit the display signal indicative of the timing predicted by the determination unit.

3. The automatic analysis device according to claim 1, wherein the control device is further configured to include a storage unit that stores a plurality of weighting coefficients obtained by quantifying an influence of each of a plurality of factors, the weighting coefficients including a first weighting coefficient relating to a type of the specimen, a second weighting coefficient relating to one or more components of the specimen, and a third weighting coefficient relating to one or more components of the reagent.

4. The automatic analysis device according to claim 3, wherein the member is one of a detection passage through which the liquid is sucked into the detection unit, and a B/F separation passage through which the liquid is sucked by the B/F separation mechanism.

5. The automatic analysis device according to claim 4, wherein the arithmetic unit determines the respective load applied to the B/F separation passage upon performing the analysis protocol of the specimen in accordance with at least one of the first weighting coefficient, the second weighting coefficient, and the third weighting coefficient.

6. The automatic analysis device according to claim 4, wherein the arithmetic unit determines the respective load applied to the detection passage upon performing the analysis protocol of the specimen in accordance with at least one of the first weighting coefficient, the second weighting coefficient, and the third weighting coefficient.

7. The automatic analysis device according to claim 3, wherein the control device is further configured to determine the second weighting coefficient in accordance with a concentration of a biological component included in the specimen detected by the detection unit.

8. A method for determining when to perform maintenance of a member in an automatic analysis device, the member contacting with at least one of a specimen, a reagent, and a liquid having the specimen and the reagent reacted with each other to a B/F separation mechanism or a detection unit, the method comprising:

performing a plurality of analysis protocols, including an analysis protocol of the specimen, where the member supplies at least one of the specimen, the reagent, and the liquid to a B/F separation mechanism or a detection unit in each of the analysis protocols, and which comes into contact with the at least one of the specimen, the reagent, and the liquid;

determining that a B/F separation process which uses the B/F separation mechanism is included in the analysis protocol of the specimen;

calculating a respective load applied to the member upon performing the analysis protocol of the specimen in accordance with the B/F separation process being included in the analysis protocol of the specimen and in accordance with properties of the specimen and the reagent in the analysis protocol of the specimen;

obtaining a total load for the analysis protocols after calculating the respective load for the analysis protocol of the specimen;

comparing the total load with a threshold value to determine when to perform the maintenance of the member; and outputting a display signal indicating to perform the maintenance of the member when the total load is determined to exceed the threshold value.

9. The method according to claim 8, wherein the respective load is calculated in accordance with a plurality of weighting coefficients quantifying an influence of each of a plurality of factors, the weighting coefficients including at least one of a first weighting coefficient relating to a type of the specimen, a second weighting coefficient relating to one or more components of the specimen, and a third weighting coefficient relating to one or more components of the reagent.

10. The method according to claim 9,
wherein the member is a B/F separation passage through which the liquid is sucked by a B/F separation mechanism that performs the B/F separation process in which a reacted component and an unreacted component are separated from the liquid, and
wherein the respective load applied to the B/F separation passage upon performing the analysis protocol of the specimen is calculated in accordance with at least one of the first weighting coefficient, the second weighting coefficient, and the third weighting coefficient.

11. The method according to claim 9,
wherein the member is a detection passage through which the liquid is sucked into the detection unit, and
wherein the second step determines the respective load applied to the detection passage upon performing the analysis protocol of the specimen in accordance with at least one of the first weighting coefficient, the second weighting coefficient, and the third weighting coefficient.

12. The method according to claim 8, further comprising:
predicting a timing when the total load exceeds the threshold value on the basis of a transition of the total load,
wherein the display signal indicative of the timing as a message to prompt a user to perform the maintenance of the member.

13. The method according to claim 10, wherein the second weighting coefficient is determined in accordance with concentration of a biological component included in the specimen detected by the detection unit.

14. The method according to claim 11, wherein the second weighting coefficient is determined in accordance with concentration of a biological component included in the specimen detected by the detection unit.

* * * * *